United States Patent [19]

Pollock

[11] 4,405,327

[45] Sep. 20, 1983

[54] METHOD FOR INHIBITING MINERALIZATION OF NATURAL TISSUE DURING IMPLANTATION

[75] Inventor: Elisabeth M. Pollock, Sandy, Utah

[73] Assignee: Extracorporeal Medical Specialties, Inc., King of Prussia, Pa.

[21] Appl. No.: 411,190

[22] Filed: Aug. 25, 1982

[51] Int. Cl.³ .............................................. A61F 1/22
[52] U.S. Cl. ........................................... 8/94.11; 3/1; 3/1.4; 3/1.5
[58] Field of Search ........................................ 8/94.11

[56] References Cited

U.S. PATENT DOCUMENTS

| | | | |
|---|---|---|---|
| 3,966,401 | 6/1976 | Hancock et al. | 8/94.11 |
| 4,050,893 | 9/1977 | Hancock et al. | 8/94.11 |
| 4,323,358 | 4/1982 | Lentz et al. | 8/94.11 |

*Primary Examiner*—Maria Parrish Tungol
*Attorney, Agent, or Firm*—Lawrence D. Schuler

[57] ABSTRACT

Natural tissues fixed with a tanning solution such as glutaraldehyde and intended for implantation in humans, e.g., porcine heart valve prosthetic devices, are treated with a solution of a water soluble quaternary ammonium salt such as dodecyltrimethylammonium chloride to inhibit mineralizaton, particularly calcification, of the tissue after implantation.

22 Claims, No Drawings

METHOD FOR INHIBITING MINERALIZATION OF NATURAL TISSUE DURING IMPLANTATION

BACKGROUND OF INVENTION

This invention relates to the preparation of natural tissue for implantation, and more particularly, to the treatment of fixed tissue to inhibit mineralization, particularly calcification, upon implantation.

Animal tissues have in recent years found wide acceptance in the preparation of various prosthetic devices for use in humans. Most notable of these is the use of porcine heart valves to replace defective mitral, tricuspid and aortic valves in humans. Also of interest is the preparation of arteries, veins and human umbilical cords for use as arterial grafts and other tubular duct replacement in humans.

Porcine heart valves have been in use for several years with generally good results. The preparation of such valves for implantation is described in the literature and in the patent art as, for example, in U.S. Pat. Nos. 3,966,401 and 4,050,893. Briefly, the valve is excised from the donor heart, trimmed and cleaned, and fixed by immersion in a tanning fluid such as a 0.2% glutaraldehyde solution. After several hours of treatment, the fixed valve is removed from the glutaraldehyde, rinsed, mounted on a stent, and stored in a glutaraldehyde solution until ready for use.

One problem which has been associated with the porcine heart valve in some individuals is calcification of the valve leaflets after an extended period of time resulting in reduced flexibility and eventual loss of efficiency in the operation of the valve. Significant calcification is readily visible in an X-ray of the affected valve.

U.S. Pat. No. 4,323,358 discloses a method for inhibiting mineralization, particularly calcification, of fixed natural tissue by treatment with a salt of a sulfated higher aliphatic alcohol such as sodium dodecyl sulfate.

It is an object of the present invention to provide another method to inhibit mineralization, and particularly calcification, of fixed natural tissue upon implantation.

It is a further object of this invention to provide a method for treatment of fixed porcine heart valve tissue to inhibit mineralization when used as a prosthetic valve replacement in humans.

These and other objects of the present invention will be apparent from the ensuing description and claims.

As used herein, the term "fixed" or "fixed tissue" refers to tissue which has been treated with a tanning solution such as 4% formaldehyde or 0.2% glutaraldehyde for a period of time and under conditions conventionally used to prepare natural tissue for implantation. The tanning process does not form any part of the present invention.

SUMMARY OF INVENTION

Natural tissue such as porcine heart valves which have been fixed for implantation in accordance with conventional procedures are treated prior to implantation with a solution of a water soluble quaternary ammonium salt whose nitrogen atom has at least one alkyl group containing from 7 to 15 carbon atoms. An example of a quaternary ammonium salt which may be used in the practice of the invention is dodecyltrimethylammonium chloride (DTMAC). The treatment may be effected in a 1% solution of DTMAC in distilled water or an aqueous electrolyte solution at ambient temperatures and for a period of 7 days. The treated tissue is removed from the DTMAC solution, rinsed, and returned to storage in steril gluteraldehyde until needed for implantation.

DESCRIPTION OF PREFERRED EMBODIMENTS

In the method of the present invention, fixed natural tissue is treated with an aqueous solution of a quaternary ammonium salt whose nitrogen atom has at least one alkyl group containing from 7 to 15 carbon atoms. Preferred quaternary ammonium salts include decyltrimethylammonium chloride, dodecyltrimethylammonium chloride and myristyltrimethylammonium chloride. Mixtures of two or more quaternary ammonium salts may be employed if desired. The quaternary ammonium salt is preferably soluble in water to a concentration (weight/volume) of a least 2%, and preferably at least 5%. The counter-ion of the quaternary ammonium compound is preferably chloride ion ($Cl^-$) but may also be, e.g., methyl sulfate ion ($CH_3SO_4-$). In the preferred embodiment, the quaternary ammonium salt is dissolved in an aqueous electrolyte solution comprising up to about 1% by weight sodium chloride, up to about 0.05% by weight each of potassium chloride, magnesium sulfate heptahydrate and dipotassium hydrogen phosphate, and up to about 0.1% by weight sodium dihydrogen phosphate. Dodecyltrimethylammonium chloride is most particularly preferred for the practice of the present invention and its use is illustrated in the following detailed example.

A DTMAC treatment solution (1% w/v) was prepared by dissolving 10 grams of dodecyltrimethylammonium chloride in a sufficient volume of an aqueous electrolyte solution (AES) to bring the total volume of treatment solution to one liter. The aqueous electrolyte solution (AES) is an aqueous solution containing approximately 0.8% by weight of sodium chloride, 0.04% by weight of potassium chloride, 0.02% by weight of magnesium sulfate heptahydrate, 0.02% by weight of dipotassium hydrogen phosphate and 0.08% sodium dihydrogen phosphate. The pH of the AES is adjusted to 7.35–7.45 with either 2 N sodium hydroxide or 2 N hydrochloric acid prior to use. The pH of the DTMAC treatment solution was 7.0.

Fifty pieces of fixed porcine valve cusp tissue weighing from about 20 to 30 mg. each were rinsed three times in AES to remove glutaraldehyde, then placed in 50 ml. of the DTMAC treatment solution at an ambient temperature of 20°–25° C. for 7 days.

After completion of the DTMAC treatment, the tissue pieces were rinsed in 0.2% glutaraldehyde solution and stored in 0.2% glutaraldehyde solution. Subsequently, the tissue pieces were sterilized for 24 hours in an aqueous solution containing 1% glutaraldehyde and 20% isopropyl alcohol, and stored in sterile 0.2% glutaraldehyde solution to await implantation.

The effectiveness of the DTMAC treatment in retarding calcification of the fixed tissue was determined by animal implant studies according to the following procedure.

Male Sprague-Dawley rats weighing 180–200 g. were anesthetized and prepared for abdominal surgery under sterile conditions. After suitable anesthetization, the abdominal area was shaved and disinfected, and a lengthwise midline skin incision approximately 4 cm. long was made in the ventral surface. The skin was separated from the underlying muscle, and three small pouches were formed in the muscle on either side of the midline incision by a small incision followed by blunt dissection of the abdominal muscle wall. One piece of DTMAC-treated tissue, rinsed in sterile saline to remove the glutaraldehyde storage solution, was inserted in each muscle pouch. The skin incision was closed and the animal returned to its cage. Implantations were made in 5 rats for a total of 30 pieces of DTMAC-treated tissue. A control group of 5 rats were implanted under identical conditions with a total of 30 pieces of fixed porcine valve cusp tissue not subjected to the DTMAC treatment.

The rats from both the control group and the DTMAC test group were sacrificed after twelve weeks and the implanted tissue examined for calcification by X-ray and by analysis for $Ca^{+2}$ levels. The entire abdominal muscle with implants in situ was excised and X-rayed. The implanted specimens were then removed and two set aside for histological examination. The remaining four implants were dissected free of surrounding tissue and extracted individually in 5 ml. of 0.6 N HCl at 70° C. for 96 hours. The extract solution was then assayed for calcium ion by atomic absorption spectrophotometry. Prior experience had established that, where tissue is analyzed and found to contain $Ca^{+2}$ levels of less than 1 μg. per mg. of wet tissue, all of the $Ca^{+2}$ so found is attributable to normal physiological processes and none is attributable to a process of mineralization. In other words, it can be concluded that no mineralization has occurred in tissue whose $Ca^{+2}$ levels are found to be less than 1 μg. per mg. of wet tissue.

The results of the animal study are presented in Table I.

TABLE I

| Rat No. | DEGREE OF CALCIFICATION | | |
|---|---|---|---|
| | X-Ray[2] | Extraction[1] | Histology[3] |
| DTMAC - Treated Porcine Cusp Tissue | | | |
| 1 | 0/6 | 0.39 ± 0.08 | 0/1* |
| 2 | 0/6 | 0.36 ± 0.05 | 0/2 |
| 3 | 0/6 | 0.39 ± 0.04 | 0/2 |
| 4 | 0/6 | 0.40 ± 0.05 | 0/1* |
| 5 | 0/6 | 0.42 ± 0.05 | —** |
| Controls: Non-DTMAC-Treated Porcine Cusp Tissue | | | |
| 1 | 4/6 | 4.02 ± 4.81 | 2/2 |
| 2 | 4/6 | 8.07 ± 6.48 | 2/2 |
| 3 | 3/6 | 4.22 ± 7.19 | 2/2 |
| 4 | 3/6 | 2.29 ± 3.3 | 2/2 |
| 5 | 2/6 | 2.51 ± 2.15 | 1/1* |

[1] Average of 4 values, μg $Ca^{++}$/mg wet wt. tissue
[2] Evaluated by visual examination; 4/6 = 4 of 6 samples evidenced a significant degree of calcification.
[3] Evaluated by visual examination of stained samples; 2/2 = 2 of 2 samples evidenced a significant degree of calcification.
*Second sample was not recovered
**Neither of the two samples was recovered Three control samples of abdominal muscle tissue were taken from each of the rats at the same time the abdominal muscle containing the implanted DTMAC-treated and non-DTMAC-treated porcine cusp tissue samples was excised from the sacrificed animals. These control samples were taken from a location in the muscle away from the site of the implanted porcine cusp tissue. The $Ca^{+2}$ levels in the abdominal muscle control samples were determined by the atomic absorption spectrophotomeric method described above. The $Ca^{+2}$ level in the abdominal muscle control samples is indicative of the amount of $Ca^{+2}$ which one would expect to find in the implanted porcine cusp tissue as a result of its exposure to the host's normal physiological processes and without the occurrence of any mineralization.

The average $Ca^{+2}$ level in the abdominal muscle control samples of the rats in whose abdominal muscle the DTMAC-treated porcine cusp tissue had been implanted was 0.27±0.06 micrograms per milligram (μg. per mg.) of wet tissue (overall average of 3 determinations on each of 5 rats). The average $Ca^{+2}$ level in the explanted DTMAC-treated porcine cusp tissue which had been implanted in the abdominal muscle was 0.39±0.05 μg. per mg. wet tissue (overall average of 4 determinations on each of 5 rats). It was concluded from this data that no mineralization had occurred in the DTMAC-treated cusp tissue. This conclusion is consistent with and supported by the X-ray and histology results set forth under the heading "DTMAC-Treated Porcine Cusp Tissue" in Table I.

The average $Ca^{+2}$ level in the abdominal muscle control samples taken from the control rats (i.e., those rats in whose abdominal muscle the non-DTMAC-treated porcine cusp tissue had been implanted) was 0.48±0.13 μg. per mg. wet tissue (overall average of 3 determinations on each of 5 rats). The average $Ca^{+2}$ level in the explanted non-DTMAC-treated porcine cusp tissue which had been implanted in the abdominal muscle of the control rats was 4.22±5.04 μg. per mg. wet tissue. It was concluded from this data that a significant degree of mineralization had occurred in the non-DTMAC-treated cusp tissue. This conclusion is consistent with and supported by the X-ray and histology results set forth under the heading "Controls: Non-DTMAC-Treated Porcine Cusp Tissue" in Table I.

As illustrated by the foregoing data, the DTMAC treatment was effective to substantially inhibit calcification of the porcine valve cusp tissue for a period of 12 weeks under the severe calcification conditions inherent in the rat test. The correlation between calcification in the rat test and human experience is such that the extensive calcification detected in the rat control group after 12 weeks would not be expected to occur in humans until after several years exposure. The DTMAC treatment would accordingly be expected to retard calcification in humans for an additional period of years beyond that normally experienced prior to the onset of calcification.

The procedure described above is one that has produced good results and constitutes a preferred embodiment of the present invention. The scope of the present invention, however, is not to be limited by the details of the described procedure, and it will be apparent to those skilled in the art that many variations in this procedure are possible. For example, the concentration of the DTMAC treatment solution may range from about 0.1 to 5.0% or higher, and other water soluble quaternary ammonium salts may be substituted for the DTMAC. Treatment temperatures may range from about 5° C. to 50° C.; and treatment times may vary from as little as 1 day to as much as 4 weeks. The quaternary ammonium salt may be dissolved in distilled water or in other so-called "balanced electrolyte solutions" whose compositions are similar to that of the AES described herein.

The pH of the treatment solution is preferably from neutral to slightly basic but may range from about 2.0 to about 10.0. Preferably the pH is about 7.0 to 7.5. Other ingredients, both active and inactive, may be utilized in combination with the water soluble quaternary ammonium salt in the treatment solution. Such variations may be developed by those skilled in the art with little or no experimentation to suit individual desires.

While the preceding example has also been limited to the treatment of porcine heart valve cusp tissue, the invention is equally applicable to the treatment of veins, arteries, and other tissues taken from pigs, other animals, or humans, all of which are known to be useful for implantation in humans. Human umbilical cords, for example, have been used as arterial grafts after fixation in glutaraldehyde. Similarly, porcine and bovine arteries and veins have also been suggested for use as arterial grafts and A-V fistula grafts. All such tissues are suitable for use in the practive of the present invention.

What is claimed is:

1. A method for inhibiting the mineralization of fixed natural tissue after implantation in a living body comprising contacting fixed natural tissue intended for implantation with an aqueous solution of a water soluble quaternary ammonium salt whose nitrogen atom has at least one alkyl group containing from 7 to 15 carbon atoms.

2. The method of claim 1 wherein the aqueous solution has a pH of from about 2.0 to about 10.0.

3. The method of claim 1 wherein the counter-ion of the quaternary ammonium salt is selected from the group consisting of chloride ion and methylsulfate ion.

4. The method of claim 1 wherein the substituent group is a straight chain aliphatic group.

5. The method of claim 1 wherein the substituent group is a branched aliphatic group.

6. The method of claim 1 wherein the water soluble quaternary ammonium salt is selected from the group consisting of decyltrimethylammonium chloride, dodecyltrimethylammonium chloride and myristyltrimethylammonium chloride.

7. The method of claim 1 wherein said natural tissue is contacted with said solution for a time sufficient to effectively inhibit future calcification of said tissue after implantation.

8. The method of claim 1 wherein said tissue is contacted with said solution for a period of at least 24 hours at ambient temperature.

9. The method of claim 1 wherein the concentration of said salt in said solution is from about 0.1 to 5% by weight.

10. The method of claim 1 wherein said solution comprises, in addition to said quaternary ammonium salt, up to about 1% by weight of sodium chloride, up to about 0.05% by weight each of potassium chloride, magnesium sulfate heptahydrate and dipotassium hydrogen phosphate, and up to about 0.1% by weight of sodium dihydrogen phospate.

11. The method of claim 1 wherein said solution comprises, in addition to said quaternary ammonium salt, about 0.8% by weight of sodium chloride, about 0.04% by weight of potassium chloride, about 0.02% by weight each of magnesium sulfate heptahydrate and dipotassium hydrogen phospate, and about 0.08% by weight of sodium dihydrogen phospate.

12. The method of claim 11 wherein the solution has a pH of about 7.

13. A method for inhibiting the calcification of fixed natural tissue after implantation in a living body which comprises contacting fixed tissue intended for implantation with a solution comprising dodecyltrimethylammmonium chloride for a time sufficient to effectively inhibit future calcification of said tissue after implantation.

14. The method of claim 13 wherein said solution comprises from about 0.1 to 5% by weight dodecyltrimethylammonium chloride.

15. The method of claim 13 wherein said tissue is contacted with said solution for a time of at least about 7 days.

16. The method of claim 13 wherein said solution comprises, in addition to said quaternary ammonium salt, up to about 1% by weight of sodium chloride, up to about 0.05% by weight each of potassium chloride, magnesium sulfate heptahydrate and dipotassium hydrogen phosphate, and up to about 0.1% by weight of sodium dihydrogen phosphate.

17. The method of claim 13 wherein said solution comprises, in addition to said quaternary ammonium salt, about 0.8% by weight of sodium chloride, about 0.04% by weight of potassium chloride, about 0.02% by weight each of magnesium sulfate heptahydrate and dipotassium hydrogen phoshpate, and about 0.08% by weight of sodium dihydrogen phosphate.

18. The method of claim 17 wherein the pH of said solution is about 7.0.

19. The method of claim 18 wherein the concentration of dodecyltrimethylammonium chloride is about 1%.

20. The method of claim 19 wherein the tissue is contacted with said solution of dodecyltrimethylammonium chloride for a period of about 7 days at ambient temperature.

21. The method of claim 13 wherein the fixed tissue is a glutaraldehyde-fixed porcine heart valve.

22. The method of claim 13 wherein said living body is a human.

* * * * *